United States Patent [19]

Vanlerberghe et al.

[11] Patent Number: 4,814,166

[45] Date of Patent: * Mar. 21, 1989

[54] POLYANIONIC COMPOUNDS, PROCESS FOR THEIR PREPARATION AND COMPOSITIONS IN WHICH THEY ARE PRESENT

[75] Inventors: Guy Vanlerberghe, Claye-Souilly; Henri Sebag, Paris, both of France

[73] Assignee: L'Oreal, Paris, France

[*] Notice: The portion of the term of this patent subsequent to May 26, 2004 has been disclaimed.

[21] Appl. No.: 867,003

[22] Filed: May 20, 1986

Related U.S. Application Data

[63] Continuation of Ser. No. 463,818, Feb. 4, 1983, abandoned.

[30] Foreign Application Priority Data

Feb. 5, 1982 [FR] France ................... 82 01908

[51] Int. Cl.$^4$ ................... A61K 7/06; C07C 149/20
[52] U.S. Cl. ................... 424/70; 424/71; 424/72; 549/417; 562/426; 562/429; 562/581; 260/501.21; 260/501.19
[58] Field of Search ................... 260/501.19, 501.21; 549/417; 562/426, 429, 581; 424/70, 71, 72, DIG. 2

[56] References Cited

FOREIGN PATENT DOCUMENTS 2486821  1/1982  France .
2027725  2/1980  United Kingdom .
2080303  2/1982  United Kingdom ............... 562/429

OTHER PUBLICATIONS

The Merck Index, 10th Edition, Merck and Co., Inc. 1983, p. 771.

*Primary Examiner*—Michael L. Shippen
*Attorney, Agent, or Firm*—Fleit, Jacobson, Cohn & Price

[57] ABSTRACT

Anionic oligomers of the general formula:

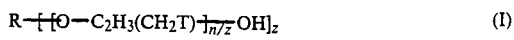

(I)

in which T denotes the radical

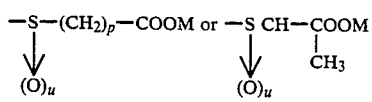

optionally in a mixture with the OH radical; $u=0$ or 1; $p=1$ or 2; $M=H$, Na, K, ammonium or a mono-, di- or tri-(alkyl or hydroxyalkyl)ammonium group, the alkyl part containing 1 to 4 carbon atoms; $n=5-30$; $z=1-6$; and R denotes an aliphatic, alicyclic, aryl, alkylaryl or aralkyl radical of valency z, which can contain 1 or more oxygen atoms, it being possible for the formula (I) to contain minor proportions of intermolecular or intramolecular branches originating from a bis-epoxide.

These oligomers are prepared by the addition of n mols of epihalogenohydrin, and optionally of a minor proportions of bis-epoxide, to 1 mol of compounds

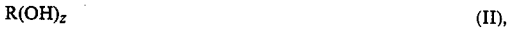 (II), in the presence of a Lewis acid, the polyhalogen compounds obtained then being converted into polythiocarboxylic compounds by reaction with a salt or an ester of thiloactic acid, thioglycolic acid or α-mercaptopropionic or β-mercaptopropionic acid, and the resulting compounds, after saponification, if appropriate, being acidified and neutralized with NaOH, KOH, NH$_4$OH or an amine, and optionally oxidized or sulphoxidized.

The compositions containing oligomers (I) are suitable for the treatment of keratin fibres, textiles and water.

34 Claims, No Drawings

POLYANIONIC COMPOUNDS, PROCESS FOR THEIR PREPARATION AND COMPOSITIONS IN WHICH THEY ARE PRESENT

This application is a continuation of application Ser. No. 463,818, filed Feb. 4, 1983, now abandoned.

The invention relates to new polyanionic oligomers, the process for their preparation and their use in cosmetic compositions.

Anionic polymers have already been proposed for cosmetic uses, in particular in lacquers or in hair care compositions.

These polymers are homopolymers or copolymers of moderate or high molecular weight, which give the style hold and have a hardening effect on the hair.

Current fashion advocates a more supple style without stiffness.

The new oligomers satisfy this requirement. They provide the style with hold, with suppleness and without a significant and overall hardening effect on the hair.

Moreover, the new anionic oligomers according to the invention have a better compatibility with the cationic polymers with which they are combined in the preferred compositions of the invention.

The cosmetic hair care compositions containing the oligomers according to the invention furthermore provide wet hair with ease of comb-out and dried hair with a more attractive general appearance.

The compounds of the invention can be represented by the following general formula (I):

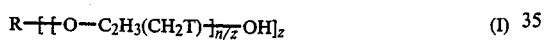  (I)

in which
T denotes the radical

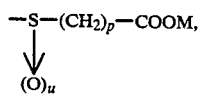

the radical

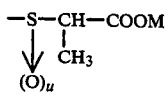

or a mixture of 50–99.5% of one of these radicals and 0.5 to 50% of the OH radical, the percentages being expressed as molar percentages;
$u$ = zero or 1;
$p$ = 1 or 2;
M denotes a hydrogen, sodium or potassium atom, an ammonium radical or a mono-, di- or tri-(alkyl or hydroxyalkyl)-ammonium group, in which the alkyl radical contains from 1 to 4 carbon atoms;
$n$ denotes an integer or decimal number from 5 to 30;
$z$ denotes an integer from 1 to 6 and preferably from 1 to 3; and
R denotes a straight-chain or branched, saturated or unsaturated aliphatic radical or an alicyclic, aryl, alkylaryl or aralkyl radical of valency $z$, which can contain from 1 to 12 oxygen atoms.

The compounds of the formula (I) can contain minor proportions of intermolecular or intramolecular branches originating from the use of bis-epoxides.

The radicals R are derived from compounds containing an alcohol or phenol group (or groups), of the formula (II):

  (II)

They act as initiators and can have a very wide variety of structures.

Amongst the alcohols and phenols of the formula (II) which can be used within the spirit of the invention, the following may be mentioned in particular as examples:
linear and branched alkanols having from 1 to 18 carbon atoms;
alkenols having 8 to 18 carbon atoms, for example undecylenyl alcohol and oleyl alcohol;
ethylene glycol alkyl ethers and diethylene glycol alkyl ethers and derivatives thereof, in particular the compounds known under the name "cellosolves" (ethylene glycol monoalkyl ethers and derivatives thereof) and under the name "carbitols" (diethylene glycol monoalkyl ethers and derivatives thereof);
ether-alcohols of the formula (IIa)

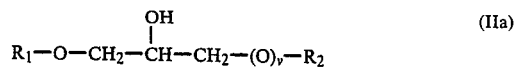  (IIa)

in which $v$=0 or 1 and $R_1$ and $R_2$ are aliphatic radicals having from 1 to 18 carbon atoms, the sum of the carbon atoms in $R_1$ and $R_2$ preferably being less than or equal to 24;
alkanols, alkenols and ether-alcohols of the formula (IIa), polyoxyethyleneated with 1 to 10 mols of ethylene oxide per mol of alchohol;
alkylene-1,2-glycols, alkylene-1,3-glycols and alkylene-α,ω-glycols having from 2 to 18 carbon atoms;
polyoxyethylene glycols and polyoxypropylene glycols having a molecular weight of less than 2,000;
polyols such as glycerol, sorbitol, pentaerythritol and glucose, optionally partially alkylated or acylated;
phenols and their unsubstituted or substituted derivatives, optionally polyoxyethyleneated with 1 to 10 mols of ethylene oxide per mol of phenol; amongst the phenol derivatives, examples which may be mentioned are bisphenols and alkylphenols, which are optionally oxyethyleneated; and
mixtures of these compounds.

The products of the formula (I) according to the invention are obtained by the polyaddition of n mols of epihalogenohydrin, such as epichlorohydrin or epibromohydrin, onto one mol of alcohol or phenol of the formula (II), in the presence of a catalyst chosen from amongst Lewis acids such as boron trifluoride, tin tetrachloride and antimony pentachloride, according to the following reaction scheme, giving rise to the formation of compounds of the formula (III)

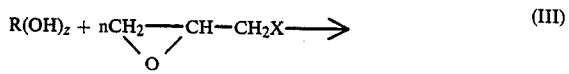  (III)

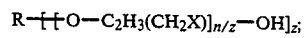

in the formula (III), X denotes Cl or Br;

n is an integer or decimal number from 5 to 30, representing an average statistical value and indicating the number of epihalogenohydrin molecules used per molecule of compound (II);

z denotes an integer from 1 to 6 and represents the number of OH equivalents in the molecule (II); and n/z represents an average statistical value and indicates the number of halogen-containing units formed in the polyether chain from each OH group.

As a result, the number of halogen-containing units formed in the polyether chain from each OH group of the alcohol $R(OH)_z$ can be less than, equal to or greater than the quotient n/z, but the total number of these halogen-containing units formed is equal to n.

As another result, the process for the preparation of the compounds of the formula (I) leads to a mixture of compounds.

The epihalogenohydrin polyaddition reaction is carried out at a temperature of between 30° and 100° C., without a solvent or in the presence of a solvent which is inert with respect to the reactants, for example in the presence of a hydrocarbon such as hexane or heptane, or in the presence of a chlorinated solvent such as methylene chloride or dichloroethane.

At the same time as the epihalogenodyrin, it is possible to add minor proportions of a bis-epoxide such as, for example, diglycidyl ether or the bisglycidyl ether of bisphenol A. The bis-epoxide will form intermolecular or intramolecular branches.

The proportions of bis-epoxide added per mol of compounds (III) are 0.5 to 5%.

The catalyst is used in proportions varying from 0,1 to 3% by weight, relative to the reaction mixture.

The polyhalogen compounds of the formula (III) are then converted to polythiocarboxylic compounds by reaction with the sodium or potassium salts of thioglycolic acid or α-mercaptopropionic or β-mercaptopropionic acid, or with the corresponding methyl or ethyl ester, and saponification of the esters obtained.

These halogen substitution reactions are carried out in the presence of NaOH or KOH if the salts of thioglycolic acid or α-mercaptopropionic or β-mercaptopropionic acid are used, and in the presence of sodium methylate or ethylate or potassium methylate or ethylate if the esters are used, in solvents which are generally alcohols such as ethanol, propanol or isopropanol, glycols such as ethylene glycol or propylene glycol, or glycol ethers such as cellosolves, diethylene glycol or dipropylene glycol, optionally in the presence of water. The reaction temperature is generally between 80° and 120° C.

If the group T represents a mixture of radicals

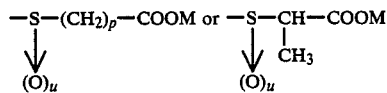

and OH, the halogen is first substituted by the radical

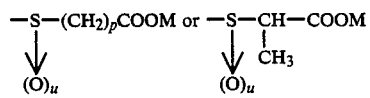

by reaction of the intermediates of the formula (III) with the salt or the ester of thioglycolic acid of α-mercaptopropionic or β-mercaptopropionic acid, as indicated above, and the halogen of the still unconverted intermediates of the formula (III) is then substituted by OH by reaction with NaOH or KOH at a temperature of 100°-120° C., or with sodium acetate or potassium acetate at a temperature of 160°-180° C., in one of the solvents indicated above which has a sufficiently high boiling point.

The products thus obtained are optionally saponified and then generally acidified and washed with water, without a solvent or in the presence of a solvent such as isopropanol, n-butanol, t-butanol or butoxyethanol.

The polycarboxylic acids are then partially or totally neutralised with NaOH, KOH, $NH_4OH$ or an aliphatic amine, and optionally subjected to steam distillation in order to deodorise them.

The aliphatic amines which can be used to neutralise the acid groups are chosen from amongst alkylamines such as mono-, di- or tri-ethylamine or mono-, di- or tri-(iso)propylamine, or alkanolamines such as mono-, di- or tri-ethanolamine, mono-, di- or tri-isopropanolamine, 2-amino-2-methylpropane-1,3-diol or 2-amino-2-methylpropan-1-ol.

The deodorising treatment can be improved by the addition of a small amount of 0.05 to 2% of a compound capable of reacting rapidly with sulphydryl compounds. Ethylene oxide and glycidol may be mentioned amongst the compounds preferred for this purpose.

The products of the formula (I) obtained according to the invention are kept in aqueous solution or isolated by evaporation to dryness, and optionally taken up in non-solvents.

These compounds can be oxidised with hydrogen peroxide at a temperature of between 20° and 50° C. to give the compounds of the formula (I) in which u denotes 1.

The invention also relates to the products obtained by the processes described above.

The invention also relates to the compositions containing a mixture of compounds of the formula (I). A composition of this type advantageously contains from 0.2 to 50% of these products. The compositions in an aqueous of aqueous-alcoholic medium can be presented in the form of solutions, gels, creams, pastes or dispersions and can be packaged in the form of aerosols to give foams or sprays.

Examples which may be mentioned of alcohols which can be used in the aqueous-alcoholic compositions are alkanols such as ethanol, isopropanol and propanol, alkoxyethanols such as cellosolves or carbitols, and glycols such as ethylene glycol, propylene glycol, butylene glycol, diethylene glycol or dipropylene glycol. The proportion of alcohol constituent in the compositions is generally from 5 to 50% by weight.

The compositions are suitable for use in the care and treatment of keratin fibres and also in a variety of industries, in particular in the textile industry of for water treatment.

When used in the care and treatment of keratin fibres, especially hair, these compositions can be, in particular, shampoos, products for facilitating styling or setting, rinse-off or leave-on lotions, products for perming or straightening, products for colouring or bleaching, and so on.

In these compositions, the following can be combined with the products of the invention: non-ionic, anionic, cationic, amphoteric and zwitterionic surfaceactive agents or mixtures thereof, anionic, cationic, amphoteric and non-ionic polymers, thickeners, agents for imparting pearlesence, foam synergistic agents or foam stabilisers, dyestuffs, colouring products, sequestering agents, preservatives, perfumes, inorganic or organic salts, reducing agents, oxidising agents, opacifiers, peptising agents, oils, waxes, natural substances, protein derivatives, anti-seborrhoea agents, anti-dandruff agents, pH modifiers and also any other substance which can have an action in the treatment or care of the hair.

The preferred compositions of the invention contain the oligomers of the formula (I) in combination with cationic polymers.

The invention also relates to a process for the treatment of keratin fibres, and especially hair, which consists in applying, to the keratin fibres, a sufficient amount of a composition such as defined above.

The invention also relates to a process for the treatment of textiles with a composition such as defined above.

The invention also relates to a process for the treatment of water with a composition containing a mixture of compounds (I).

The invention will be illustrated with the aid of the non-limiting examples below.

EXAMPLE 1

Preparation of a mixture of compounds of the general formula (I) in which R denotes the divalent radical:

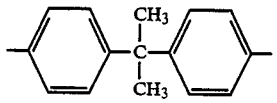

$z = 2$
$n = 15$
$T = $ —S—CH$_2$—COOM, in which M=H or Na (a) Preparation of a mixture of polyhalogen compounds of the formula (III)

34.2 g of bisphenol A (0.15 mol) are dispersed in 60 ml of dichloroethane at 50° C. 0.85 ml of BF$_3$/ether complex is then added, after which 208 g of epichlorohydrin (2.25 mols) are added dropwise in the course of 1 hour. Stirring is continued for 1 hour at 50°–60° C. and the solvent is evaporated off. Functional group analysis is used to check that all the epoxide groups have reacted.

(b) Preparation of a mixture of compounds of the formula (I)

143 g of thioglycolic acid containing 10.5 milliequivalents/g (that is to say 1,500 milliequivalents of carboxyl groups) are neutralised with 309 g of 40% strength NaOH solution under a nitrogen atmosphere.

161.5 g of the product obtained by the process described above (1,500 milliequivalents of chlorine), solubilised in 80 g of methylcellosolve (ethylene glycol methyl ether), are then introduced at 80° C. in the course of 45 minutes. The reaction mixture is then heated for 2 hours at 100° C. The degree of completion of the reaction, assessed by determining the remaining sulphydryl groups, is of the order of 96%.

The mixture is diluted with 300 g of water and then acidified by the addition of 265 ml of 6N hydrochloric acid (1,590 milliequivalents).

The organic phase is decanted and washed twice with 250 g of water at 70° C. About 50 g of butoxyethanol or isopropanol can be added during the first decantation in order to fluidise the organic phase.

150 g of water and 130 g of 40% strength NaOH solution are then added. The solvent is driven off under reduced pressure and the residue is taken up in water so as to give, after total removal of the butoxyethanol, a solution containing about 41% of active ingredients. This solution is in the form of a clear, light yellow liquid with a pH of the order of 9. The basicity index is 2.32 milliequivalents/g (determination of the carboxylate group).

EXAMPLE 2

Preparation of a mixture of compounds of the general formula (I) in which R denotes the divalent radical:

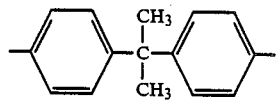

$z = 2$
$n = 15$

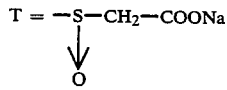

13 ml of hydrogen peroxide of 200 volumes strength (60% strength by weight) are added to 100 g of the solution obtained according to Example 1 (220 milliequivalents of thioether), at a temperature of 35° C. in the course of 30 minutes.

The stirring and the temperature are maintained for 5 hours and the solution is then left to stand for 48 hours at ambient temperature.

The solution obtained is almost colourless and contains virtually no more peroxides.

EXAMPLE 3

Preparation of a mixture of compounds of the general formula (I) in which R denotes the divalent radical:

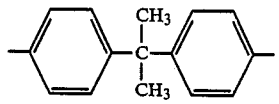

$z = 2$
$n = 15$
T denotes —OH and —S—CH$_2$—COONa in the proportions 50/50.

28.6 g of thiogylcolic acid (300 milliequivalents of acid) are neutralised with 60 g of 40% strength of NaOH solution (600 milliequivalents). 25 g of sodium acetate (306 milliequivalents) are then added to this mixture, after which 64.5 g of the polychlorine compounds obtained according to Example 1 (a), solubilised beforehand in 70 g of diethylene glycol, are added dropwise at 80° C.

The reaction mixture is heated for 3 hours at 100° C. and then progressively up to 180° C., the water being removed by evaporation. The mixture is thus heated at this temperature for 3 hours.

The reaction mixture is taken up in 50 g of water and 30 g of 40% strength NaOH solution for 1 hour at 70° C.

The resulting mixture is then evaporated to dryness and the residue is taken up in isopropanol to remove the last traces of solvents. The precipitate is filtered off, drained and dried.

The product thus obtained is in the form of a sandy-coloured powder which is prefectly soluble in water. The basicity index is 2.3 milliequivalents/g.

EXAMPLE 4

Preparation of a mixture of compounds of the general formula (I) in which R represents the divalent radical:

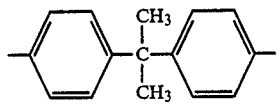

$z=2$
$n=20$
$T=-S-CH_2-COOM$, in which $M=H$ or Na (a) Preparation of a mixture of polyhalogen compounds of the formula (III)

0.95 ml of tin tetrachloride is added to 22.8 g of bisphenol A (0.1 mol), dispersed in 30 g of dichloroethane, after which 185 g of epichlorohydrin (2 mols) are added at 50° C. in the course of 2 hours. The reaction is complete after stirring for 1 hour after the addition has ended.

The solvent is removed by heating under reduced pressure and the organic phase is washed three times with 220 ml of water at 90° C. After drying, the product obtained is in the form of a very thick, sticky oil.

(b) Preparation of a mixture of compounds of the formula (I)

153 g of the above product (1,500 milliequivalents of chlorine) and 148 g of thioglycolic acid (1,500 milliequivalents of acid) are dissolved in 150 g of 96° strength ethanol under a nitrogen atmosphere.

300 g of 40% strength NaOH solution are then introduced in the course of 10 minutes. The reaction is exothermic and the temperature rises rapidly from 25° C. to 75° C.

The mixture is heated for 2 hours under reflux, the ethanol is then distilled and the residue is taken up in water so as to be in a homogeneous medium.

The resulting mixture is heated again for 2 hours at 100° C. It is acidified by the addition of 125 ml of concentrated hydrochloric acid.

The compounds of the formula (I) in the acid form separate out from the aqueous phase. 80 g of n-butanol are added.

The organic phase is decanted and washed with water at 80°–90° C. 270 g of 20% strength NaOH solution are added and the solvent is then evaporated off under reduced pressure, water being added in proportion at the same time, so as to give, at the end, a thick colourless aqueous solution containing 70% of active ingredients. Basicity index: 3.9 milliequivalents/g.

EXAMPLE 5

Preparation of a mixture of compounds of the general formula (I) in which R denotes the divalent radical:

$-CH_2-CH_2-O-CH_2-CH_2-$ $z=2$
$n=15$
$T=-S-CH_2-COOM$, in which $M=H$ or Na (a) Preparation of a mixture of polyhalogen compounds of the formula (III)

0.39 ml of BF$_3$ etherate is added to 15.9 g of diethylene glycol (0.15 mol), after which 208 g (2.25 mols) of epichlorohydrin are added at 55° C. in the course of 2 hours. (0.17 ml of BF$_3$ etherate is added approximately two-thirds of the way through the addition.)

The mixture is heated for a further 2 hours after the addition has ended. The degree of completion of the reaction is then virtually quantitative.

(b) Preparation of a mixture of compounds of the formula (I)

105 g of thioglycolic acid (1,090 milliequivalents of acid groups) are dissolved in 30 g of absolute ethanol.

220 g of 40% strength NaOH solution are then added thereto in the course of about 15 minutes, the temperature being allowed to rise virtually to the reflux temperature.

104.5 g of the polyhalogen compounds prepared above (1,050 milliequivalents of chlorine), diluted with 70 g of absolute ethanol, are then introduced dropwise.

The mixture is thus heated for 4 hours under reflux.

The reaction medium is diluted with 120 ml of water and then acidified with 200 ml of 6N hydrochloric acid.

After the addition of 80 ml of n-butanol, the organic phase is decanted and then washed twice with 200 ml of water at 80° C.

The organic phase is neutralised with 150 g of NaOH containing 5.7 milliequivalents/g, and the solvent is distilled, water being added in order to complete the removal of the latter.

This gives a thick, light brown-coloured liquid containing 80% of active ingredients. Basicity index: 4.5 milliequivalents/g.

EXAMPLE 6

Preparation of a mixture of compounds of the general formula (I) in which R denotes the divalent radical:

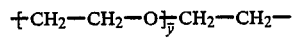

$y=3$ (y represents a statistical value)
$z=2$
$n=24$
$T=-S-CH_2-COOM$, $M=H$ or Na (a) Preparation of a mixture of polyhalogen compounds of the formula (III)

0.4 ml of BF$_3$ etherate is added to 12 g (0.06 mol) of polyethylene glycol of MW (molecular weight) 200 (PEG 200), after which 133.2 g of epichlorohydrin (1.44 mols) are added at 50° C. in the course of 2 hours.

(b) Preparation of a mixture of compounds of the formula (I)

290 g of 40% strength NaOH solution are added to 137 g of thioglycolic acid (1,440 milliequivalents of acid), after which the product obtained above, diluted with 50 g of methylcellosolve, is added at 80° C. The reaction mixture is then heated at 100° C. for 2 hours.

The solvent is distilled by azeotropic distillation. The treatment is finished by steam distillation. The final solution is clear and yellow-coloured. Proportion of active ingredients: 33.5%. Basicity index: 1.9 milliequivalents/g.

EXAMPLE 7

Preparation of a mixture of compounds of the general formula (I) in which R denotes the divalent radical:

$z = 2$
$n = 16$
$T = -S-CH_2-COOM$, M=H or Na (a) Preparation of a mixture of polyhalogen compounds of the formula (III)

7.1 g (0.05 mol) of hexane-1,6-diol are dissolved in 20 ml of dichloroethane. 0.3 ml of $BF_3$/acetic acid acomplex is added, after which 89 g of epichlorohydrin (0.96 mol) are added at 50° C.

2 hours after the addition has ended, the solvent is removed by heated under reduced pressure.

(b) Preparation of a mixture of compounds of the formula (I)

195 g of 40% strength NaOH solution (1,950 milliequivalents) are added to 91.4 g of thioglycolic acid (960 milliequivalents of acid) under a nitrogen atmosphere, after which the mixture of polychlorine compounds obtained above, diluted with 50 ml of butylcellosolve, is added at 80° C.

The reaction mixture is then heated for 4 hours at 100° C.

It is acidified by the addition of 83 ml of concentrated hydrochloric acid, and the organic phase is separated off and then washed twice with water at 90° C.

The polyanionic acids thus obtained are neutralised with 69 g of 40% strength NaOH solution, and the butylcellosolve is distilled under reduced pressure.

The residue is taken up in water and the mixture is then subjected to steam distillation.

This gives 275 g of an aqueous solution containing 37.7% of active ingredients and having a basicity index of 2.3 milliequivalents/g.

To remove the residual traces of mercaptans, 0.9 g of glycidol is added and dispersed by stirring for 15 minutes.

EXAMPLE 8

Preparation of a mixture of compounds of the general formula (I) in which:
R denotes the divalent radical:

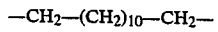

$z = 2$
$n = 20$
$T = -S-CH_2-COOM$, in which M=H or Na (a) Preparation of a mixture of polyhalogen compounds of the formula (III)

0.4 ml of $BF_3$ etherate is added to 8.1 g (0.04 mol) of dodecane-1,12-diol, dissolved in 20 ml of dichloroethane, after which 74 g of epichlorohydrin (0.8 mol) are added at 50° C. in the course of 1 hour 15 minutes. After stirring for 1 hour, the solvent is removed by evaporation under reduced pressure.

(b) Preparation of a mixture of compounds of the formula (I)

The product thus obtained is taken up in 50 g of ethylcellosolve and the mixture is run dropwise, in the course of 30 minutes, at 80° C., into a solution of sodium thioglycolate prepared from 73.5 g of thioglycolic acid (770 milliequivalents of acid groups) and from 155 g of 40% strength NaOH solution.

The reaction mixture is heated at 100° C. for 5 hours.

66 ml of concentrated hydrochloric acid are then added, after which 50 ml of isopropanol are added at 70° C.

The organic phase is decanted and washed with water.

The solvent is then removed by evaporation.

The mixture of polyanionic compounds thus obtained has a weight of 101 g and an acid index of 5.18 milliequivalents/g. It is neutralised by the addition of 104 g of 20% strength NaOH solution and deodorised by stem distillation.

This finally gives a clear, light yellow solution containing 25.5% of active ingredients and having a basicity index of 1.4 milliequivalents/g.

EXAMPLE 9

Preparation of a mixture of compounds of the general formula (I) in which:
R denotes the monovalent radical $C_{12}H_{25}-$
$z = 1$
$n = 15$
$T = -S-CH_2-COOM$, in which M=H or Na (a) Preparation of the polyhalogen compounds of the formula (III)

0.3 ml of $BF_3$ etherate is added to 11.1 g of molten dodecan-1-ol (0.06 mol), after which 83.2 g of epichlorohydrin (0.9 mol), to which 11.16 g of the bisglycidyl ether of bisphenol A containing 5.37 milliequivalents/g of epoxide groups (that is to say 0.03 mol) have been added, are added at 70° C. in the course of 1 hour 30 minutes.

After stirring for 1 hour, the reaction is not totally finished. A further 0.1 ml of $BF_3$ etherate is added and the mixture is heated for a further 1 hour.

(b) Preparation of a mixture of compounds of the formula (I)

107 g of ethyl thioglycolate (855 milliequivalents of sulphydryl groups) are added to 100 g of the polyhalogen compounds prepared in this way (854 milliequivalents of chlorine), under a nitrogen atmosphere, after which 152 g of sodium methylate containing 5.64 milliequivalents/g are added dropwise at 65°-70° C. The mixture is heated for 4 hours under reflux. The degree of completion of the reaction is then 99%.

After dilution with 100 ml of water, 45 g of 40% strength NaOH solution are added and the mixture is heated for 2 hours at 70° C.

It is then acidified with 100 ml of 12N HCl.

After the addition of 50 ml of n-butanol, the organic phase is separated off and then washed with water at 90° C.

The polyanionic compounds thus obtained are neutralised with 20% strength NaOH solution, and the solvent is removed by heating under reduced pressure, water being added at the same time.

The final blackcurrant-coloured solution obtained contains 29% of active ingredients and the basicity index is 1.48 milliequivalents/g.

EXAMPLE 10

Preparation of a mixture of compounds of the general formula (I) in which:

R denotes the divalent radical:

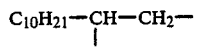

z=2
n=20
T=—S—CH$_2$—COOM, in which M=H or K.

(a) Preparation of a mixture of polyhalogen compounds of the formula (III)

0.4 ml of BF$_3$ etherate is added to 8.1 g (0.04 mol) of dodecane-1,2-diol, after which 74 g of epichlorohydrin (0.8 mol) are added at 50° C. in the course of 1 hour 15 minutes.

The temperature and the stirring are maintained for a further 1 hour.

(b) Preparation of a mixture of compounds of the formula (I)

98 g of ethyl thioglycolate (800 milliequivalents of sulphydryl groups) are added to the product thus obtained, after which 200 g of sodium methylate in methanol, containing 5.64 milliequivalents/g, are added in the course of 2 hours 30 minutes at 65°–70° C.

The mixture is heated under reflux for 4 hours. It is then acidified by the addition of 75 ml of 12N hydrocholoric acid and diluted with 50 ml of isopropanol.

The organic phase containing the polyanionic compounds is decanted, separated off and then washed twice with hot water. It is neutralised by the addition of 102 g of 30% strength KOH solution and the isopropanol is distilled with water.

After removal of the solvent, about 100 g of water are passed through in order to deodorise the product.

This finally gives a blackcurrant-coloured aqueous solution containing 30% of active ingredients and having a basicity index of 1.5 milliequivalents/g.

EXAMPLE 11

Preparation of a mixture of compounds of the general formula (I) in which:

R denotes the trivalent radical:

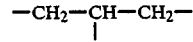

Z=3
n=15
T=—S—CH$_2$—COOM, M=H or Na.

(a) Preparation of a mixture of polychlorine compounds (III)

0.4 ml of BF$_3$ etherate is added to 92 g of glycerol (0.08 mol), after which 111 g (1.2 mols) of epichlorohydrin are added dropwise.

The stirring and the heating are maintained for 2 hours after the introduction has ended.

(b) Preparation of a mixture of compounds of the formula (I)

113 g of thioglycolic acid (1,190 milliequivalents of acid) are mixed with 238 g of 40% strength NaOH solution under a nitrogen atmosphere, and 117 g of the above product, diluted with 50 ml of methylcellosolve, are then added at a temperature of 80° C in the course of 45 minutes.

The reaction mixture is then heated for 3 hours at 100° C. and the solvent is subsequently evaporated off by heating under reduced pressure and removed completely by azeotropic distillation. The solution obtained is clear and light yellow-coloured. The concentration of active ingredients is 31% and the basicity index is 1.75 milliequivalents/g.

EXAMPLE 12

Mixture of compounds of the general formula (I) in which R denotes the tetravalent radical:

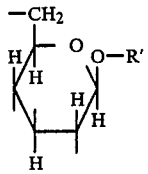

in which R' denotes a mixture of C$_8$ and C$_{10}$ alkyl radicals in the proportions 50/50 z=4
n=8
T=—S—CH$_2$—CH$_2$—COOM, in which M=H, Na or H$^\oplus$N(CH$_2$—CH$_2$OH)$_3$ (a) Preparation of a mixture of polyhalogen compounds of the formula (III)

Preparation of a mixture of alkylglucosides.

2 ml of 10% strength sulphuric acid are added to 888 g (12 mols) of butanol, after which 360 g (2 mols) of glucose are added in the course of 1 hour at a temperature of 80° C., with stirring. The heating is then continued at 110° C. for 5 hours, the butanol and the water being distilled at the same time.

A mixture composed of 377 g (2.9 mols) of octan-1-ol and 458 g (2.9 mols) of decan-1-ol is then added to the reaction medium in the course of 1 hour 30 minutes at a temperature of 90° C., the butanol being distilled off at the same time under 100 mm Hg.

The heating is continued until the butanol and the butylglucoside have been totally removed.

200 g of the mixture thus obtained are run into 2 liters of acetone. Part of the mixture precipitates and is filtered off.

The filtrate is heated at 80° C. under a pressure of 40 mm Hg in order to evaporate off the acetone, and then at 110° C. under a pressure of 2 mm Hg in order to remove the excess fatty alcohols. 34.6 g of a brown water-soluble wax, consisting essentially of octylglucoside and decylglucoside, are thus collected.

0.1 ml of BF$_3$ etherate is added to 9.2 g (0.03 mol) of the alkylglucosides thus obtained, dissolved in 30 ml of 1,2-dichloroethane, after which 22.2 g (0.24 mol) of epichlorohydrin are added dropwise at 50° C.

When the reaction is finished, the solvent is removed by heating under reduced pressure.

(b) Preparation of a mixture of compounds of the formula (I)

48 g of a 40% strength aqueous solution of sodium hydroxide are added to 25.4 g of β-mercaptopropionic acid (0.24 mol), dissolved in 50 ml of water, after which the above mixture of polychlorine compounds, solubilised in 50 ml of cellosolve beforehand, is added at 80° C. in the course of 1 hour. The heating is then contined for 2 hours at 100° C.

The mixture is acidified by the addition of 23 ml of hydrochloric acid and diluted with 300 ml of water at 60° C.

The organic phase is decanted, washed and dried under reduced pressure.

This gives a thick brown-coloured oil which is soluble in water in the presence of NaOH or triethanolamine.

The acid index is 4.1 milliequivalents/g.

EXAMPLE 13

Mixture of compounds of the general formula (I) in which R denotes the radical:

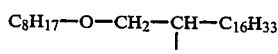

$z=1$
$n=12$
$T=-S-CH_2-COOM$, in which $M=H$, Na or

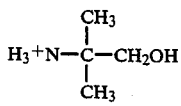

(a) Preparation of a mixture of polychlorine compounds of the formula (III)

The alcohol of the formula (IIa) is prepared by adding 268 g of 1,2-epoxyoctadecane (1 equivalent of epoxide group), at a temperature of 150° C., to 390 g (3 mols) of n-octanol in the presence of 8.5 g of sodium methylate in methanol (0.005 mol).

The addition lasts 2 hours. After heating for a further 3 hours, the excess octanol is removed under reduced pressure and the compound (IIa) is then distilled at a temperature of 193°–205° C. under a pressure of 1 mm Hg.

After cooling, it is in the form of a white wax having a melting point of 48°–49° C.

Preparation of the polychlorine derivatives.

1.5 ml of BF$_3$ etherate are added to 159 g (0.4 mol) of the compound thus obtained, after which 444 g (4.8 mols) of epichlorohydrin are added dropwise at 50°–55° C.

Halfway through the addition, a further 0.9 ml of BF$_3$ etherate is added. The addition lasts 2 hours 30 minutes.

After heating for a further 1 hour, this gives a brown-coloured oil.

(b) Preparation of a mixture of compounds of the formula (I)

200 g of a 40% strength aqueous solution of NaOH are added to 95.3 g of thioglycolic acid (1 equivalent) under a nitrogen atmosphere, after which 125.5 g (1 equivalent of chlorine) of the compounds obtained above, solubilised in 75 g of ethylcellosolve (ethylene glycol ethyl ether), are added dropwise at 80° C.

The reaction medium is then heated for 4 hours at 100° C. It is acidified by the addition of 165 ml of hydrochloric acid after having been diluted with 250 ml of water.

50 ml of butoxyethanol are added and the organic phase is separated off and washed a further two times with 200 ml of water at 80° C.

The reaction mixture is soluble in water in the presence of NaOH or 2-amino-2-methylpropan-1-ol.

85 g of a 40% strength aqueous solution of NaOH (0.85 mol) are added and the solvent is distilled under reduced pressure, water being added in proportion.

This finally gives a brown aqueous solution containing 35% of active ingredients and having a basicity index of 1.7 milliequivalents/g.

EXAMPLE 14

Preparation of a mixture of compounds of the general formula (I) in which:

R denotes the monovalent oleyl radical:

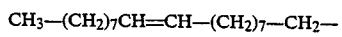

$z=1$
$n=5$
$T=S-CH_2-COOM$, in which $M=H$ or Na (a) Preparation of a mixture of polychlorine compounds of the formula (III)

0.45 ml of boron trifluoride etherate is added to 68.3 g of oleyl alcohol (0.25 mol), after which 115.6 g of epichlorohydrin (1.25 mols) are added dropwise at between 50° and 55° C. Duration of the addition: 2 hours.

After 30 minutes, the reaction is finished.

The reaction mixture is in the form of a viscous brown liquid.

(b) Preparation of a mixture of compounds of the formula (I)

130.5 g (1.23 mols) of sodium hydroxide containing 9.86 milliequivalents/g are added to 58.5 g of thioglycolic acid (0.625 mol) under a nitrogen atmosphere.

91.3 g of the mixture of polychlorine compounds obtained above are then added at 80° C. in the course of 45 minutes. The temperature is raised to 100° C. and 70 g of methyl cellosolve are added after 30 minutes.

After heating for 2 hours 30 minutes, the degree of completion of the reaction is 95%.

200 g of water are added to the reaction mixture and the resulting mixture is acidified by the addition of 70 g of hydrochloric acid (0.69 equivalent).

The organic phase is separated off by decantation and is taken up in 200 g of water and 40 g of isopropanol.

50 g of sodium hydroxide containing 9.86 milliequivalents/g and 50 g of water are added to the washed organic phase, and the isopropanol and a large part of the water are distilled without evaporating to dryness.

15

The final solution is adjusted to 30% of active ingredients. (COO⁻ index: 1.4 milliequivalents/g).

The solution thus obtained is clear and golden yellow-coloured.

EXAMPLE 15

Preparation of a mixture of compounds of the formula (I) in which:

R denotes the monovalent nonylphenol radical:

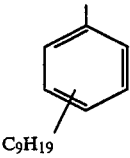

$z=1$
$n=8$
$T=$

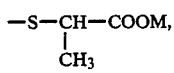

in which M=H or Na (a) Preparation of a mixture of polychlorine compounds of the formula (III)

0.48 ml of boron trifluoride/ether complex is added to 44 g of nonylphenol (0.2 mol), after which 148 g of epichlorohydrin (1.6 mols) are added at 50°-55° C. in the course of 2 hours 30 minutes.

This gives a viscous greenish-coloured liquid.

(b) Preparation of a mixture of compounds of the formula (I)

44.6 g of thiolactic (α-mercaptopropionic) acid (0.4 equivalent of SH groups) are neutralised by the addition, under a nitrogen atmosphere, of 84 g of sodium hydroxide solution containing 9.86 milliequivalents/g.

43 g of the mixture obtained above, dissolved in 25 g of methylcellosolve, are then added at 80° C. in the course of 20 minutes, and the reaction mixture is heated at 100° C. for 3 hours 30 minutes.

It is acidified by the addition of 50 g of concentrated hydrochloric acid in 100 g of water, and the organic phase is separated off and then washed with 200 g of hot water in the presence of a small amount of isopropanol.

The mixture of polycarboxylic compounds is neutralised with 32.5 g of aqueous sodium hydroxide solution (0.32 mol), the remaining isopropanol is distilled and the concentration of the final solution is adjusted to 45% of active ingredients.

COO⁻ index: 2.1 milliequivalents/g.

APPLICATION EXAMPLES

Example A1

The shampoo having the following composition is prepared:

| | |
|---|---|
| Mixture of compounds according to Example 9 | 0.9 g |
| Surface-active agent of the formula:<br>R—CHOH—CH₂O—[CH₂—CHOH—CH₂—O]ₙH | 5 g |

$R = C_9$-$C_{12}$ alkyl

16 n = average statistical value of 3.5

Mixture of glucoside alkyl ethers corresponding to the theoretical formula:

| | |
|---|---|
| [structure shown] | 15 g | in which n is equal to 0, 1, 2, 3 or 4
R = linear $C_8$-$C_{10}$ alkyl
marketed with a content of 30% of active ingredients under the name TRITON CG 110 by SEPPIC

| | |
|---|---|
| NaCl | 4 g |
| Piperazine/epichlorohydrin polycondensate with a molecular weight of 1,500 to 2,000 | 1 g |
| Preservative q.s. (quantity sufficient) | |
| Perfume q.s. | |
| Dyestuff q.s. | |
| HCl q.s. pH 7.3 | |
| Water q.s.p. | 100 g |

Example A2

The shampoo having the following composition is prepared:

| | |
|---|---|
| Mixture of compounds according to Example 10 | 1.2 g |
| Sodium salt of sulphated alkanol ($C_{12}$-$C_{14}$) oxyethyleneated with 2.2 mols of ethylene oxide, containing 25% of active ingredient | 40 g |
| Alkyl($C_{12}$-$C_{18}$)-dimethylcarboxymethylammonium hydroxide containing 30% of active ingredient, sold under the name DEHYTON AB30 by HENKEL | 25 g |
| NaCl | 4 g |
| Cationic polymer consisting of repeat units of the formula | 0.5 g |

$$\left[ \begin{array}{cc} CH_3 & CH_3 \\ | & | \\ {}^{\oplus}N-(CH_2)_3-{}^{\oplus}N-(CH_2)_6 \\ | & | \\ CH_3 \; Cl^{\ominus} & CH_3 \; Cl^{\ominus} \end{array} \right]$$

| | |
|---|---|
| Preservative q.s. | |
| Perfume q.s. | |
| Dyestuff q.s. | |
| NaOH q.s. pH 7 | |
| Water q.s.p. | 100 g |

Example A3

The shampoo having the following composition is prepared:

| | |
|---|---|
| Mixture of compounds according to Example 7 | 0.4 g |
| Compound of the formula:<br>$CH_3-(CH_2)_{11}CH_2-(OCH_2CH_2)_6-OCH_2COOH$<br>containing 90% of active ingredient, sold under the name SANDOPAN DTC Acid by SANDOZ | 12 g |
| Triethanolamine salt of the condensation product of copra fatty acids and animal protein hydrolysate, containing 40% of active ingredients, sold under the name MAYPON 4CT by STEPAN | 11 g |
| NaCl | 4 g |
| Quaternised cellulose sold under the name J.R. 400 by UNION CARBIDE | 0.8 g |
| Preservative q.s. | |

-continued

| | |
|---|---|
| Perfume q.s. | |
| Dyestuff q.s. | |
| NaOH q.s. for pH 7.4 | |
| Water q.s.p. | 100 g |

Example A4

A rinse-off hair lotion having the following composition is prepared:

| | |
|---|---|
| Mixture of compounds of Example 8 | 2 g |
| Dimethyldiallylammonium chloride/acrylamide copolymer with a molecular weight of more than 500,000, containing 8% of active ingredient, sold under the name MERQUAT 550 by MERCK | 3 g |
| NaCl | 4 g |
| Preservative q.s. | |
| Perfume q.s. | |
| Dyestuff q.s. | |
| NaOH q.s.p. pH 6.1 | |
| Water q.s.p. | 100 g |

Example A5

A rinse-off lotion having the following composition is prepared:

| | |
|---|---|
| Mixture of compounds of Example 11 | 0.7 g |
| Mixture of cetyl/stearyl alcohols and cetyl/stearyl alcohols oxyethyleneated with 15 mols of ethylene oxide | 3 g |
| Hydroxyethylcellulose sold under the name CELLOSIZE QP 4400 H by UNION CARBIDE | 0.6 g |
| Quaternary polyvinylpyrrolidone copolymer having a molecular weight of about 1 million, marketed under the name GAFQUAT 755 by GENERAL ANILINE | 0.5 g |
| Distearyldimethylammonium chloride | 0.3 g |
| NaCl | 4 g |
| Preservative q.s. | |
| Perfume q.s. | |
| Dyestuff q.s. | |
| HCl q.s. pH 7.2 | |
| Water q.s.p. | 100 g |

Example A6

An "after-shampoo" composition in the form of an aerosol foam and having the following composition is prepared:

| | |
|---|---|
| Mixture of compounds according to Example 8 | 2 g |
| Quaternised cellulose, sold under the name JR 400 by UNION CARBIDE | 1 g |
| Distearyldimethylammonium chloride | 0.4 g |
| NaCl | 4 g |
| Preservative q.s. | |
| Perfume q.s. | |
| Dyestuff q.s. | |
| HCl q.s. pH 7.3 | |
| Water q.s.p. | 100 g |
| The aerosol cans are filled with the following: | |
| Composition above | 90 g |
| FREON 114/12 (43/57) | 10 g |
| Total | 100 g |

Example A7

A shampoo having the following composition is prepared:

| | |
|---|---|
| Mixture of compounds according to Example 1 | 1.2 g |
| Non-ionic surface-active agent of the formula | 10 g |

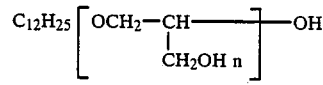

n = average statistical value of 4.2

| | |
|---|---|
| Preservative q.s.p. | |
| Perfume q.s. | |
| Dyestuff q.s. | |
| NaOH q.s. pH 6.8 | |
| Water q.s.p. | 100 g |

Example A8

A shampoo having the following composition is prepared:

| | |
|---|---|
| Mixture of compounds according to Example 6 | 1.8 g |
| Triethanolamine alkyl($C_{12-14}$)—sulphate containing 40% of active ingredient | 25 g |
| Preservative q.s. | |
| Perfume q.s. | |
| Dyestuff q.s. | |
| NaOH q.s. pH 7.5 | |
| Water q.s.p. | 100 g |

Example A9

A setting lotion having the following composition is prepared:

| | |
|---|---|
| Mixture of compounds of Example 1 | 1 g |
| 60/40 vinylpyrrolidone/vinyl acetate copolymer sold under the name "PVP/PA S 630" by GAF | 0.5 g |
| Water q.s.p. | 100 ml |

Example A10

A setting lotion having the following composition is prepared:

| | |
|---|---|
| Mixture of compounds of Example 1 | 0.8 g |
| Quaternised vinylpyrrolidone copolymer having a molecular weight of about 100,000, sold under the name "Gafquat 734" by GAF | 1.5 g |
| Ethyl alcohol | 48 g |
| Water q.s.p. | 100 ml |

Example A11

This example is identical to Example A10 except that the mixture of compounds according to Example 1 is replaced by the same weight of the mixture of compounds according to Example 2.

Example A12

A setting lotion having the following composition is prepared:

| | |
|---|---|
| Mixture of compounds of Example 1 | 2 g |
| Silicone oil sold under the name Huile Rhodorsil 70646 by Rhone-Poulenc | 0.3 g |

-continued

| | |
|---|---|
| Ethyl alcohol | 8 g |
| Water q.s.p. | 100 ml |

Example A13

This example is identical to Example A12 except that the mixture of compounds according to Example 1 is replaced by the same weight of the mixture of compounds according to Example 5.

Example A14

A reducing agent for perming having the following composition is prepared:

| | |
|---|---|
| Mixture of compounds of Example 1 | 1.0 g |
| Thioglycolic acid | 6.0 g |
| Thiolactic acid | 3.0 g |
| 20% strength ammonia solution | 10.0 g |
| Ammonium bicarbonate | 6.0 g |
| Diethylenetriaminepentaacetic acid | 0.4 g |
| Oleyl alcohol polyoxyethyleneated with 20 mols of ethylene oxide | 1.0 g |
| Protein hydrolysate | 0.5 g |
| Perfume q.s. | |
| Dyestuff q.s. | |
| Opacifier q.s. | |
| Deionised water q.s.p. | 100 ml |

Example A15

This example is identical to Example A14 except that the mixture of compounds according to Example 1 is replaced by the same weight of the mixture of compounds according to Example 3.

Example A16

A reducing agent for perming having the following composition is prepared:

| | |
|---|---|
| Mixture of compounds of Example 1 | 2.0 g |
| Sodium bisulphite | 4.0 g |
| Ammonium sulphite | 3.0 g |
| Monoethanolamine | 4.0 g |
| Ethylenediaminetetraacetic acid | 0.3 g |
| Nonylphenol polyoxyethyleneated with 9 mols of ethylene oxide | 1.0 g |
| Perfume q.s. | |
| Dyestuff q.s. | |
| Opacifier q.s. | |
| Deionised water q.s.p. | 100 ml |

Example A17

A reducing agent for perming having the following composition is prepared:

| | |
|---|---|
| Mixture of compounds of Example 1 | 1.0 g |
| Thioglycolic acid | 7.0 g |
| 20% strength ammonia solution | 6.0 g |
| Monoethanolamine | 1.0 g |
| Ammonium bicarbonate | 3.0 g |
| Ethylenediaminetetraacetic acid | 0.5 g |
| Cationic polymer consisting of repeat units of the formula: | 1.0 g |

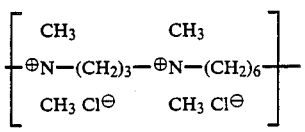

| | |
|---|---|
| Oleyl alcohol polyoxyethyleneated with 20 mols of ethylene oxide | 1.0 g |
| Perfume q.s. | |
| Dyestuff q.s. | |
| Opacifier q.s. | |
| Deionised water q.s.p. | 100 ml |

Example A18

A reducing agent for perming having the following composition is prepared:

| | |
|---|---|
| Mixture of compounds of Example 1 | 1.0 g |
| Thioglycolic acid | 5.0 g |
| Ammonium bicarbonate | 5.0 g |
| Diethylenetriaminepentaacetic acid | 0.3 g |
| Oleyl alcohol polyoxyethyleneated with 20 mols of ethylene oxide | 1.0 g |
| Perfume q.s. | |
| Dyestuff q.s. | |
| Opacifier q.s. | |
| Deionised water q.s.p. | 100 ml |

Example A19

A fixing agent for perming having the following composition is prepared:

| | |
|---|---|
| Mixture of compounds of Example 1 | 1 g |
| Hydrogen peroxide q.s. 8 volumes strength | |
| Stabilisers | 0.1 g |
| Citric acid q.s. pH 3.5 | |
| Perfume q.s. | |
| Peptising agent q.s. | |
| Opacifier q.s. | |
| Dyestuff q.s. | |
| Demineralised water q.s.p. | 100 ml |

Example A20

A fixing agent for perming having the following composition is prepared:

| | |
|---|---|
| Mixture of compounds of Example 1 | 0.5 g |
| Hydrogen peroxide q.s. 8 volumes strength | |
| Stabilisers | 0.1 g |
| Amidoalkylbetaine containing 100% of active ingredient, sold under the name "Tego Betaine L7" by Goldsmith | 0.5 g |
| Citric acid q.s. pH 4 | |
| Perfume q.s. | |
| Peptising agent q.s. | |
| Opacifier q.s. | |
| Dyestuff q.s. | |
| Demineralised water q.s.p. | 100 ml |

Example A21

This example is identical to Example A20 except that the mixture of compounds according to Example 1 is replaced by the same weight of the mixture of compounds according to Example 4.

Example A22

The dyeing formulation having the following composition is prepared:

| | |
|---|---|
| Mixture of compounds of Example 14 | 4 g |
| 1-N—methylamino-2-nitro-4-N—di-(hydroxyethyl)-aminobenzene | 0.6 g |
| Nonylphenyl oxyethyleneated with 4 mols of ethylene oxide, sold under the name "REMCOPAL 334" by GERLAND | 8 g |
| Nonylphenol oxyethyleneated with 9 mols of ethylene oxide, sold under the name "REMCOPAL 349" by GERLAND | 8 g |
| Hydrochloric acid q.s.p. pH = 10 | |
| Water q.s.p. | 100 g |

This composition is in the form of a fluid gel which is applied easily to the hair; when applied to bleached hair, it imparts thereto, after an interval of 20 minutes followed by rinsing and drying, a uniform, light parma violet colour.

Example A23

The shampoo having the following composition is prepared:

| | |
|---|---|
| Mixture of compounds of Example 15 | 1 g |
| Non-ionic surface-active agent of the formula R—CHOH—CH$_2$O—O$\{$CH$_2$—CHOH—CH$_2$—O$\}_n$H) R = C$_9$-C$_{12}$ alkyl n = 3.5 | 10 g |
| Acetic acid q.s.p. pH = 7 | |
| Water q.s.p. | 100 g |

We claim:

1. Mixture of anionic compounds of the formula

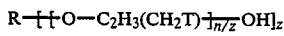  (I)

in which:

T denotes the radical

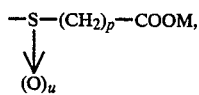

the radical

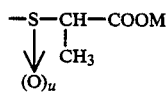

or a mixture of 50–99.5% of one of these radicals and 0.5 to 50% of the OH radical, the percentages being expressed as molar percentages;
u=0 or 1;
p=1 or 2;
M denotes a hydrogen, sodium or potassium atom, an ammonium radical or a mono-, di- or tri-(alkyl or hydroxyalkyl)-ammonium group, in which the alkyl radical contains from 1 to 4 carbon atoms;
n denotes an integer of decimal number from 5 to 30;
z denotes an integer from 1 to 6; and
R is the same as the radical R in a compound containing an alcohol or phenol groups (or groups), of the formula:

R(OH)$_z$ selected from:
 linear or branched alkanols having from 1 to 18 carbon atoms;
 alkenols having from 8 to 18 carbon atoms;
 ethylene glycol alkyl ethers and diethylene glycol alkyl ethers;
 alkanols, alkenols and ether-alcohols of the formula (IIa)

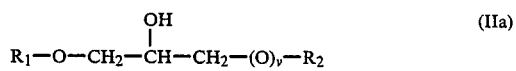

polyoxyethyleneated with 1 to 10 mols of ethylene oxide per mol of alcohol;
 alkylene-1,2-glycols, alkylene-1,3-glycols or alkylene-α,ω-glycols having from 2 to 18 carbon atoms;
 polyoxyethylene glycols or polyoxypropylene glycols having a molecular weight of less than 2000;
 polyols,
 partially aalkylated or acylated polyols; and
 phenols and their unsubstituted or substituted derivatives, optionally polyoxyethyleneated with 1 to 10 molecules of ethylene oxide per molecule of phenol;
molecules of ethylene oxide per molecule of phenol; optionally formula (I) containing minor proportions of intermolecular or intramolecular branches originating from a bis-epoxide.

2. Mixture of compounds according to claim 1, wherein the compound containing an alcohol or phenol group (or groups) is a polyol selected from glycerol, sorbitol, pentaerythritol and glucose, optionally partially alkylated or acylated, or bisphenols and alkylphenols optionally polyoxyethyleneated with 1 to 10 mols of ethylene oxide per mol of phenol.

3. A composition obtained by a process which comprises the steps of:
 (i)(a) subjecting an epihalogenohydrin to a polyaddition with a compound of the formula (II)

  (II), in which R and z are as defined in claim 1, in an amount of n mols of epihalogenohydrin per mol of compound of formula (II), in the presence of a Lewis acid catalyst, at a temperature of 30°–100° C. and in the absence of a solvent or in the presence of a solvent which is inert with respect to the reactants to obtain a mixture of intermediates of the formula (III)

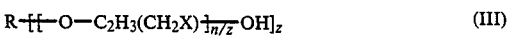  (III)

in which X denotes Cl or Br, or
 (b) subjecting epihalogenohydrin and a minor proportion of diglycidyl ether or bis glycidyl ether of bis phenol A to a polyaddition with a compound of the formula (II)

  (II), in which R and z are as defined in claim 1, in an amount of n mols of epihalogenohydrin per mol of compound of formula (II), in the presence of a Lewis acid catalyst, at a temperature of 30°–100° C. and in the absence of a solvent or in the presence of a solvent which is inert with respect to the reactant to obtain a mixture of intermediate compounds, the proportion of diglycidyl ether or bis-glycidyl ether of bis phenol A added being from 0.5 to 5 mol % per mol of intermediate compounds (ii) converting the intermediate compounds (I) into carboxyl compounds of the formula (I) in which T denotes

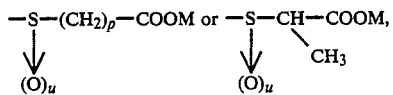

in which p and M are as defined in claim 1 and u=0 by reaction at a temperature of 80°–120° C., in the presence of an alcoholic solvent and optionally in the presence of water, with the sodium or potassium salt of thioglycolic, α-mercaptopropionic of β-mercaptopropionic acid in the presence of NaOH or KOH, or with the corresponding methyl or ethyl esters in the presence of sodium methylate or ethylate or potassium methylate or ethylate, and saponification of the esters obtained, or (II) into compounds of the formula (I) in which T denotes 50 to 99.5 mol % of one of the radicals

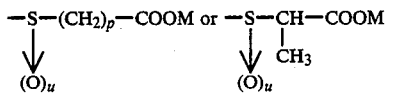

and 0.5 to 50 mol % of OH radical, by reaction firstly of the intermediate compounds with thioglycolic, α-mercaptopropionic or β-mercaptopropionic acid as specified in paragraph (I) above, and then by reaction with NaOH or KOH at a temperature of 100°–120° C. or with sodium acetate or potassium acetate at 160°–180° C., in the presence of a suitable solvent, and after saponification, if appropriate, acidifying the products thus obtained partially or totally neutralising the polycarboxylic acids obtained with NaOH, KOH, NH$_4$OH or an aliphatic amine, and optionally deodorising the partially or totally neutralised compounds by steam distillation and/or by the addition of a compound reacting with the sulphydryl compounds; and (iii) optionally oxidising the thioether group of the compounds obtained to a sulphoxide group, in the presence of hydrogen peroxide, to give the compounds of the formula (I) in which u=1, and an aqueous or aqueous-alcoholic vehicle.

4. A composition according to claim 3 wherein, in stage (i), an inert solvent is used which is selected from hydrocarbons and chlorinated solvents.

5. A composition according to claim 3 wherein, in stage (ii), a solvent is used which is selected from alkanols and glycols.

6. A composition according to claim 3 wherein the Lewis acid catalyst used is selected from boron trifluoride, tin tetrachloride and antimony pentachloride.

7. A composition according to claim 5 wherein, in stage (i), the compound of the formula $$R(OH)_z \qquad (II)$$

is selected from
linear or branched alkanols having from 1 to 18 carbon atoms, alkenols having from 8 to 18 carbon atoms, ethylene glycol alkyl ethers or diethylene glycol alkyl ethers;
alkanols, alkenols and ether-alcohols of the formula (IIa)

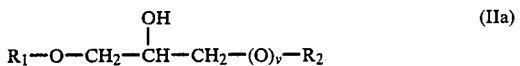

polyoxyethyleneated with 1 to 10 mols of ethylene oxide per mol of alcohol;
alkylene-1,2-glycols, alkylene-1,3-glycols or alkylene-α,ω-glycols having from 2 to 18 carbon atoms;
polyoxyethylene glycols or polyoxypropylene glycols having a molecular weight of less than 2000;
polyols optionally partially alkylated or acylated; and
phenols and their unsubstituted or substituted derivatives,
optionally polyoxyethyleneated with 1 to 10 molecules of ethylene oxide per molecule of phenol.

8. A cosmetic composition suitable for the treatment of human hair, which composition comprises, in an aqueous or aqueous-alcoholic medium, from 0.2 to 50% by weight of a mixture of compounds as claimed in claim 1.

9. A composition according to claim 8 which is in the form of a solution, a gel, a cream, a paste or a dispersion or is packaged in the form of an aerosol.

10. A composition according to claim 8 which is an aqueous-alcoholic solution containing from 5 to 50% by weight of an alcohol selected from ethanol, isopropanol, propanol, ethylene glycol, propylene glycol, butylene glycol, diethylene glycol, dipropylene glycol, glycol monoethyl ether and diethylene glycol monoethyl ether.

11. A cosmetic composition according to claim 8 which also contains at least one constituent selected from non-ionic, anionic, cationic, amphoteric and zwitterionic surface-active agents, anionic, cationic, amphoteric and non-ionic polymers, thickeners, agents for imparting pearlescence, foam synergistic agents, foam stabilisers, sequestering agents, preservatives, perfumes, inorganic or organic salts, reducing agents, oxidising agents, opacifiers, peptising agents, oils, waxes, protein derivatives, and pH modifiers.

12. A process for the treatment of human hair which process comprises the step of applying to the hair a suitable amount of a composition as claimed in 8.

13. Mixture of compounds according to claim 1, wherein the compound containing an alcohol or phenol group (or groups) is a polyol selected from glycerol, sorbitol, pentaerythritol and glucose, optionally partially alkylated or acylated, or bisphenols and alkylphenols optionally polyoxyethyleneated with 1 to 10 mols of ethylene oxide per mol of phenol.

14. Mixture of compounds obtained by a process which comprises the steps of
(i)(a) subjecting an epihalogenohydrin to a polyaddition with a compound of the formula (II)

$$R(OH)_z \qquad (II)$$

in which R and z are as defined in claim 1, in an amount of n mols of epihalogenohydrin per mol of compound of formula (II), in the presence of a Lewis acid catalyst, at a temperature of 30°–100° C. and in the absence of a solvent or in the presence of a solvent which is inert with respect to the reactants to obtain a mixture of intermediates of the formula (III)

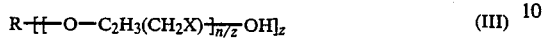   (III)

in which X denotes Cl or Br, or
(b) subjecting epihalogenohydrin and a minor proportion of bis-epoxide to a polyaddition with a compound of the formula (II)

$R(OH)_z$   (II)

in which R and z are as defined in claim 12, in an amount of n mols of epihalogenohydrin per mol of compound of formula (II), in the presence of a Lewis acid catalyst, at a temperature of 30°–100° C. and in the absence of a solvent or in the presence of a solvent which is inert with respect to the reactant to obtain a mixture of intermediate compounds, the proportion of bis-epoxide added being from 0.5 to 5 mol% per mol of intermediate compounds
(ii) converting the intermediate compounds
(I) into carboxyl compounds of the formula (I) in which T denotes

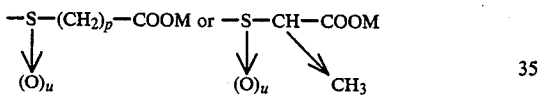

in which p and M are as defined in claim 12 and u=0 by reaction at a temperature of 80°–120° C., in the presence of an alcoholic solvent and optionally in the presence of water, with the sodium or potassium salt of thioglycolic, α-mercaptopropionic or β-mercaptopropionic acid in the presence of NaOH or KOH, or with the corresponding methyl or ethyl esters in the presence of sodium methylate or ethylate or potassium methylate or ethylate, and saponification of the esters obtained, or
(II) into compounds of the formula (I) in which T denotes 50 to 99.5 mol% of one of the radicals

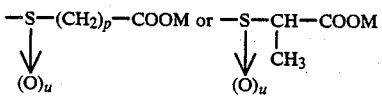

and 0.5 to 50 mol% of OH radical, by reaction firstly of the intermediate compounds with thioglycolic, α-mercaptopropionic or β-mercaptopropionic acid as specified in paragraph (I) above, and then by reaction with NaOH or KOH at a temperature of 100°–120° C. or with sodium acetate or potassium acetate at 160°–180° C., in the presence of a suitable solvent, and after saponification, if appropriate, acidifying the products thus obtained partially or totally neutralizing the polycarboxylic acids obtained with NaOH, KOH, NH4OH or an aliphatic amine, and optionally deodorising the partially or totally neutralised compounds by steam distillation and/or by the addition of a compound reacting with the sulphhydryl compounds, and
(iii) optionally oxidising the thioether group of the compounds obtained to a sulphoxide group, in the presence of hydrogen peroxide, to give the compounds of the formula (I) in which u=1.

15. Mixture of compounds according to claim 14 wherein, in stage (i), an inert solvent is used which is selected from hydrocarbons and chlorinated solvents.

16. Mixture of compounds according to claim 14 wherein, in stage (ii), a solvent is used which is selected from alkanols and glycols.

17. Mixture of compounds according to claim 14 wherein the Lewis acid catalyst used is selected from boron trifluoride, tin tetrachloride and antimony pentachloride.

18. Mixture of compounds according to claim 14 wherein, in stage (i), the compund of the formula $R(OH)_z$   (II)

is selected from
linear or branched alkanols having from 1 to 18 carbon atoms, alkenols having from 8 to 18 carbon atoms, ethylene glycol alkyl ethers or diethylene glycol alkyl ethers;
alkanols, alkenols and ether-alcohols of the formula (IIa)

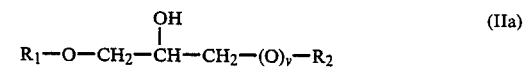

polyoxyethyleneated with 1 to 10 mols of ethylene oxide per mol of alcohol;
alkylene-1,2-glycols, alkylene-1,3-glycols or alkylene-α,ω-glycols having from 2 to 18 carbon atoms;
polyoxyethylene glycols or polyoxypropylene glycols having a molecular weight of less than 2000;
polyols optionally partially alkylated or acylated; and
phenols and their unsubstituted or substituted derivatives, optionally polyoxyethyleneated with 1 to 10 molecules of ethylene oxide per molecule of phenol.

19. A cosmetic composition suitable for the treatment of human hair, which composition comprises, in an aqueous or aqueous-alcoholic medium, from 0.2 to 50% by weight of a mixture of compounds as claimed in claim 1.

20. A composition according to claim 19 which is in the form of a solution, a gel, a cream, a paste or a dispersion or is packaged in the form of an aerosol.

21. A composition according to claim 19 which is an aqueous-alcoholic solution containing from 5 to 50% by weight, of an alcohol selected from ethanol, isopropanol, propanol, ethylene glycol, propylene glycol, butylene glycol, diethylene glycol, dipropylene glycol, glycol monoethyl ether and diethylene glycol monoethyl ether.

22. A cosmetic composition according to claim 19 which also contains at least one constituent selected from non-ionic, anionic, cationic, amphoteric and zwitterionic surface-active agents, anionic, cationic, amphoteric and non-ionic polymers, thickeners, agents for imparting pearlescence, foam synergistic agents, foam stabilisers, dyestuffs, sequestering agents, preservatives, perfumes, inorganic or organic salts, reducing agents, oxidising agents, opacifiers, peptising agents, oils, waxes, natural substance, protein derivatives, and pH modifiers.

23. A process for the treatment of human hair which process comprises the step of applying to the hair a suitable amount of a composition as claimed in claim 19.

24. Mixture of compounds according to claim 1 wherein R denotes the divalent radical:

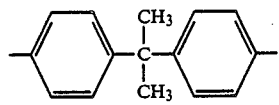

$z=2$, $n=15$, and $T=-S-CH_2-COOM$.

25. Mixture of compounds according to claim 1 wherein R denotes the divalent radical:

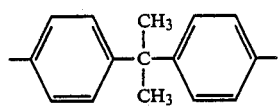

$z=2$, $n=15$, and

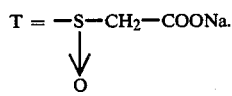

26. Mixture of compounds according to claim 1 wherein R denotes the divalent radical:

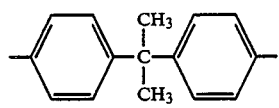

$z=2$, $n=15$, and T denotes $-OH$ and $-S-CH_2-COONa$ in the proportions 50/50.

27. Mixture of compounds according to claim 1 wherein R denotes the divalent radical:

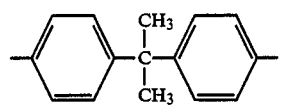

$z=2$, $n=20$, and $T=-S-CH_2-COOM$.

28. Mixture of compounds according to claim 1 wherein R denotes the divalent radical:

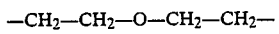

$z=2$, $n=15$, and $T=-S-CH_2-COOM$.

29. Mixture of compounds according to claim 1 wherein R denotes the divalent radical:

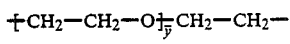

$y=3$ (y represents a statistical value), $z=2$, $n=24$, and $T=-S-CH_2-COOM$.

30. Mixture of compounds according to claim 1 wherein R denotes the divalent radical:

$z=2$, $n=16$, and $T=-S-CH_2-COOM$.

31. Mixture of compounds according to claim 1 wherein R denotes the divalent radical:

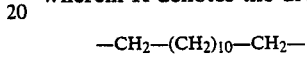

$z=2$, $n=20$, and $T=-S-CH_2-COOM$.

32. Mixture of compounds according to claim 1 wherein R denotes the divalent radical:

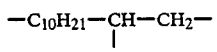

$z=2$, $n=20$, and $T=-S-CH_2-COOM$.

33. Mixture of compounds according to claim 1 wherein R denotes the trivalent radical:

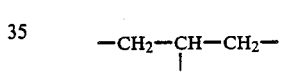

$z=3$, $n=15$, and $T=-S-CH_2-COOM$.

34. Mixture of compounds according to claim 1 wherein R denotes the tetravalent radical:

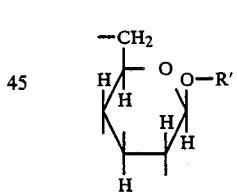

in which R' denotes a mixture of $C_8$ and $C_{10}$ alkyl radicals in the proportions 50/50, $z=4$, $n=8$, and $T=-S-CH_2-CH_2-COOM$.

* * * * *